United States Patent
Wickert

(10) Patent No.: US 6,632,661 B2
(45) Date of Patent: Oct. 14, 2003

(54) SELF-SPREADING MICROBIOLOGICAL CULTURE DEVICE

(75) Inventor: Peter D. Wickert, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 428 days.

(21) Appl. No.: 09/732,002

(22) Filed: Dec. 7, 2000

(65) Prior Publication Data

US 2002/0072114 A1 Jun. 13, 2002

(51) Int. Cl.[7] .............................................. C12M 1/22
(52) U.S. Cl. ...................... 435/305.4; 435/30; 435/31; 435/32; 435/34; 435/287.4; 435/287.7; 435/287.8; 435/288.3
(58) Field of Search ................................ 435/4, 30–32, 435/34, 287.4, 287.7, 287.8, 287.9, 288.3, 305.4

(56) References Cited

U.S. PATENT DOCUMENTS

| | | | | |
|---|---|---|---|---|
| 3,881,993 A | * | 5/1975 | Freake et al. ............. 435/287.7 |
| 4,241,181 A | * | 12/1980 | Lund ............................ 435/34 |
| 4,565,783 A | * | 1/1986 | Hansen et al. ............ 435/305.1 |
| 5,137,812 A | * | 8/1992 | Matner ......................... 435/38 |
| 5,232,838 A | * | 8/1993 | Nelson et al. ................. 435/30 |
| 5,284,753 A | * | 2/1994 | Goodwin, Jr. ................ 435/30 |
| 5,443,963 A | * | 8/1995 | Lund ............................ 435/34 |
| 5,496,706 A | * | 3/1996 | Kuusela et al. ............. 435/7.33 |
| 6,022,682 A | * | 2/2000 | Mach et al. .................... 435/4 |
| 6,391,626 B1 | * | 5/2002 | Adams et al. ............ 435/287.9 |

FOREIGN PATENT DOCUMENTS

WO WO 99/32601 7/1999 ............ C12M/1/20

OTHER PUBLICATIONS

US 4,476,226, 10/1984, Hansen et al. (withdrawn)

* cited by examiner

*Primary Examiner*—David A. Redding
(74) *Attorney, Agent, or Firm*—Christopher D. Gram; Nancy M. Lambert

(57) ABSTRACT

A device for culturing microorganisms and its use are described. The claimed device comprises a substrate having a top side, a pedestal mounted on the top side of the substrate and comprising a non-absorbent culture surface, a flexible cover sheet attached to the substrate and comprising a bottom surface, the cover sheet being configured to cover the culture surface, and a culture medium deposited on one or more surfaces selected from: the culture surface, and the cover sheet bottom surface. An aqueous sample is spread and contained by the claimed device without additional equipment or manipulation by the end user.

20 Claims, 2 Drawing Sheets

SELF-SPREADING MICROBIOLOGICAL CULTURE DEVICE

FIELD OF THE INVENTION

The present invention provides a device for growing microorganisms configured to spread an aqueous sample to cover a designated culture surface. The end user is able to obtain a uniformly spread sample without any additional equipment or manipulation of the sample.

BACKGROUND OF THE INVENTION

Media for culturing microorganisms are generally prepared by dispersing a solidifying agent in an aqueous solution containing nutrients and other ingredients necessary for the growth of specific microorganisms. Conventional solidifying agents, such as agar, are often inconvenient for the end user. Agar medium is typically prepared in bulk, sterilized, then melted in boiling water or by exposure to flowing steam. The hot agar must be carefully cooled to approximately 45° C. before it can be poured into petri dishes. The cooled, but still liquefied, medium is aliquoted, poured into the petri dish containing the microbiological sample, mixed with the sample and allowed to solidify. After the agar hardens, the plates are incubated at a prescribed temperature for a prescribed period of time. After incubation, the number and variety of colonies growing in each dish is counted by visual inspection. In this way, one can determine the number and variety of microorganisms or colony-forming units present in an aqueous sample.

A dry culture medium device is disclosed in U.S. Pat. No. 4,565,783, entitled "Dry Culture Media," granted to Hansen (the '783 patent). The device of the '783 patent comprises a bottom member with an adhesive coating and a further coating of cold-water-soluble powder adhered uniformly to the adhesive coating. The powder comprises one or more ingredients such as a gelling agent, one or more nutrients, or a mixture thereof. A preferred embodiment further comprises a cover sheet releasably adhered to at least a portion of the bottom member.

A shortcoming of the device disclosed in the '783 patent is that there is no means by which one can control the dispersion of an aqueous sample deposited on the bottom member. If one simply allows the aqueous sample to spread on its own, the result may be an inoculum of irregular shape and dimension. Such irregularity can lead to less-than-optimum concentrations of culture medium components, e.g., gelling agents, nutrients, inhibitors, indicators, and the like. Also, one risks having the aqueous sample spread beyond the boundary of the bottom member, thereby spilling culture liquid, creating mess and potentially contaminating the work area. Alternatively, one may employ a sample-restraining device to restrain spreading of the sample. An example of a device suitable for this purpose comprises a block with a cavity exposed on one surface. An aqueous sample is applied to the bottom member of the device disclosed in the '783 patent, the cover sheet is lowered over the sample and the sample-restraining block is placed on the cover sheet with the cavity side down. The walls of the cavity define the extent to which the sample is allowed to spread. The sample-restraining block is removed after the gelling agent of the device begins to gel. This process is cumbersome because when culturing a large number of samples, one must either have a large supply of sample-restraining blocks or wait for each sample to begin to gel before proceeding to the next culture.

The '783 patent also discloses an embodiment of the device that employs a spacer attached to the upper surface of the substrate. The spacer has a hole cut in its center that forms a well of predetermined size, shape and volume that is designed to confine the culture medium following hydration. However, there may be disadvantages in utilizing a device having such a sample well. For example, the sample volume may be inadequate to completely fill the well so that there is an undesirable air space between the surface of the liquid sample and the lowered cover sheet. Or, alternatively, the sample volume may be so great that the sample overflows the well upon lowering the cover sheet upon the liquid sample surface. If the sample reaches the top of the well, it will flow over the surface of the spacer through the narrow gap between the top surface of the spacer and the top sheet.

U.S. Pat. No. 6,022,682, entitled, "Article and Method for Detection of Enterotoxigenic Staphylococci," granted to Mach et al. (the '682 patent) teaches the use of a disc-shaped article for detecting or confirming the presence of thermostable nuclease positive, potentially enterotoxigenic staphylococci in a sample. The article contains a chemical composition specific for the detection of specific strains of staphylococci. The article is particularly adapted for detecting the presence of enterotoxigenic staphylococci such as *S. aureus* in a pre-grown, gel-based bacterial culture. However, the article of the '682 patent is not an integral part of or attached to a dry culture device, is not designed to receive a liquid aqueous sample, and is removable from the dry culture device during use.

What is needed is a device for growing microorganisms that, without additional labor or equipment required of the end user, a) limits the spread of a liquid sample so that the sample does not spill, and b) results in a spread sample that is uniformly shaped and sized.

SUMMARY OF THE INVENTION

The present invention provides a device for growing microorganisms that facilitates spreading of an aqueous sample uniformly, to substantial homogeneity, and with reduced risk of spilling, with no additional effort or manipulation by the end user.

In several places throughout the specification, guidance is provided through lists of examples. In each instance, the recited list serves only as a representative group and should not be interpreted as an exclusive list.

The present invention provides a device for growing microorganisms comprising a substrate having a top side, a pedestal mounted on the top side of the substrate and comprising a non-absorbent culture surface, a flexible cover sheet attached to the substrate and comprising a bottom surface, and a culture medium deposited on one or more surfaces selected from the culture surface and the cover sheet bottom surface.

In another aspect, the present invention also provides a method of growing microorganisms in which the end user is not required to manipulate the aqueous sample after plating in order to obtain a spread sample area of substantially uniform size and shape.

The present invention provides a method of culturing microorganisms comprising providing a device for growing microorganisms comprising a substrate having a top side, a pedestal mounted on the top side of the substrate and comprising a non-absorbent culture surface, a flexible cover sheet attached to the substrate and comprising a bottom surface, and a culture medium deposited on one or more surfaces selected from the culture surface and the cover sheet bottom surface; placing a sample on the culture surface; covering the sample with the cover sheet; and incubating the device.

In yet another aspect, the present invention provides a method of detecting microorganisms, wherein the method of culturing microorganisms described above further comprises detecting the microorganisms.

DETAILED DESCRIPTION OF THE INVENTION

The present invention provides a device for growing microorganisms configured to spread an aqueous sample to cover a designated culture surface. The end user is able to obtain a uniformly spread sample without any additional equipment or manipulation of the sample.

Figure 1:
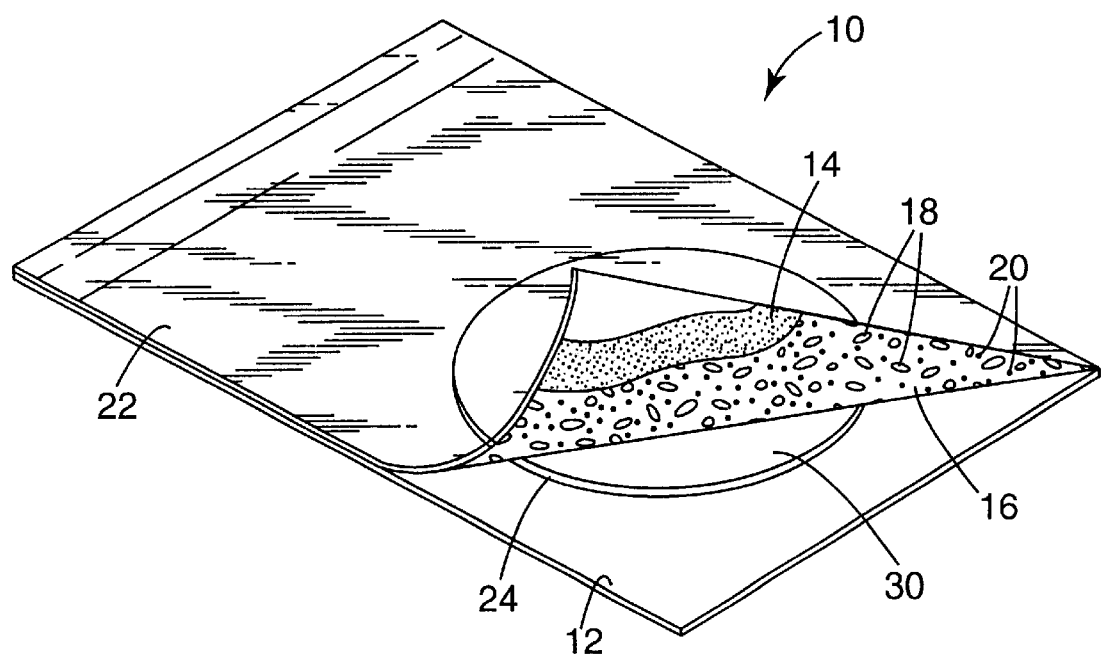
FIG. 1 is a top perspective view of one embodiment of the invention.
Figure 2:
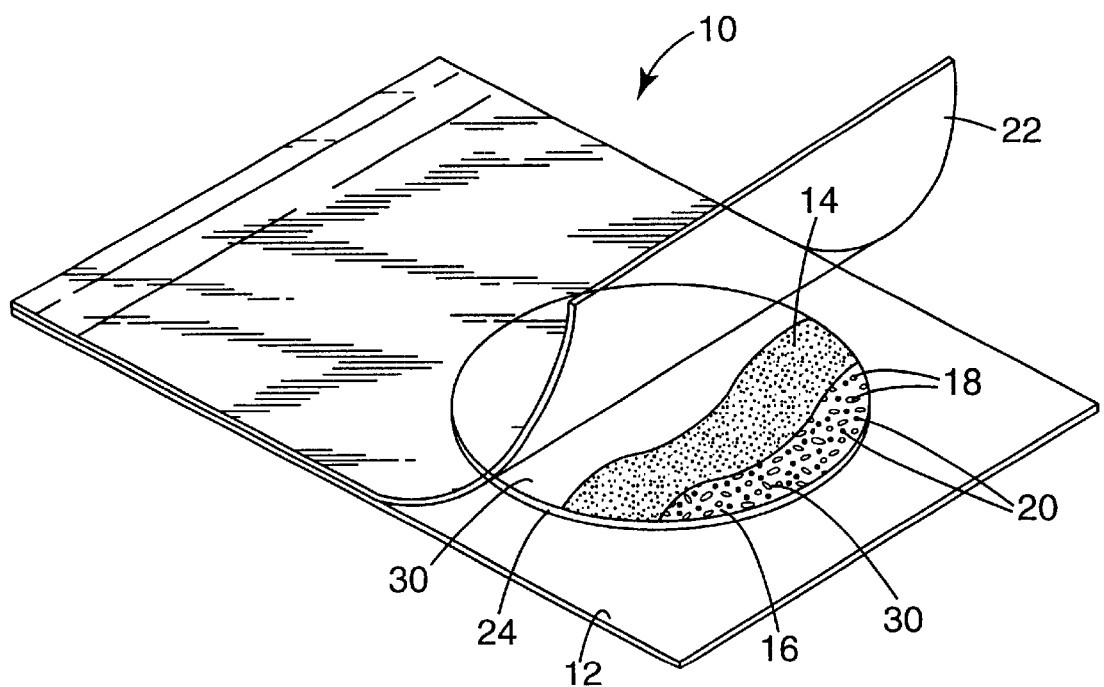
FIG. 2 is a top perspective view of a second embodiment of the invention.

The claimed device 10 is shown in the accompanying figures. The device 10, as shown in FIGS. 1 and 2, comprises a substrate 12 that acts as a support for the pedestal 24. The pedestal 24 may be mounted on (e.g., adhered) to the top side of the substrate 12 or the pedestal 24 and substrate 12 may be formed as a single unit. The pedestal has a non-absorbent culture surface 30 for receiving an aqueous sample. The device also comprises a flexible cover sheet 22 that is attached to the substrate and is configured so that the cover sheet may cover the culture surface 30. A culture medium 16 that is soluble in cold water is deposited on the culture surface 30 (as shown in FIG. 2), the bottom surface of the cover sheet 22 (as shown in FIG. 1), or both. The culture medium 16 is cold-water-soluble and comprises a gelling agent 18, one or more nutrients 20, or any combination thereof. The culture medium 16 may comprise one or more nutrients 20 selected to promote the growth of bacteria, fungi, molds, or other microorganism. The culture medium 16 may further comprise one or more indicators to aid in detecting microorganisms that have grown in the sample. The culture medium 16 may still further comprise one or more antibiotics selected to inhibit growth of one or more types of bacteria, fungi, molds or other microorganisms.

The substrate 12 may be flexible or rigid. In one embodiment, the substrate 12 comprises a film of a material such as polyester, polypropylene or polystyrene. Other suitable materials for the substrate 12 include paper or cardboard, which may or may not be treated with a waterproof coating. More broadly, the substrate may comprise any rigid or flexible material that will not interfere with the growth of microorganisms on the culture surface 30. The substrate 12 may be transparent or opaque. A transparent substrate 12 and pedestal 24 allow one to observe colonies of microorganisms through the substrate and pedestal.

The pedestal 24 rises above and is mounted on the top side of the substrate 12. The pedestal 24 may be formed separately from the substrate 12 and then attached to the top side of the substrate. In such an embodiment, the pedestal 24 and the substrate 12 may be formed from the same or different materials. The pedestal 24 may be attached to the substrate 12 by any suitable means such as, for example, with an adhesive or by mechanical means. Alternatively, the pedestal 24 and substrate 12 may be formed as a single, continuous unit. Accordingly, as used herein, "mounted on the top side of the substrate" means that the pedestal 24 is attached to the substrate 12 and includes embodiments in which the pedestal 24 is attached to the substrate 12 because they are formed as a single continuous unit as well as any embodiment in which the pedestal 24 is affixed to the substrate 12, such as with an adhesive. The pedestal may be any suitable shape such as the disc shown in FIG. 1. Whatever the shape of the pedestal 24, the culture surface 30 should be substantially co-planar with the top side of the substrate 12.

Figure 3:
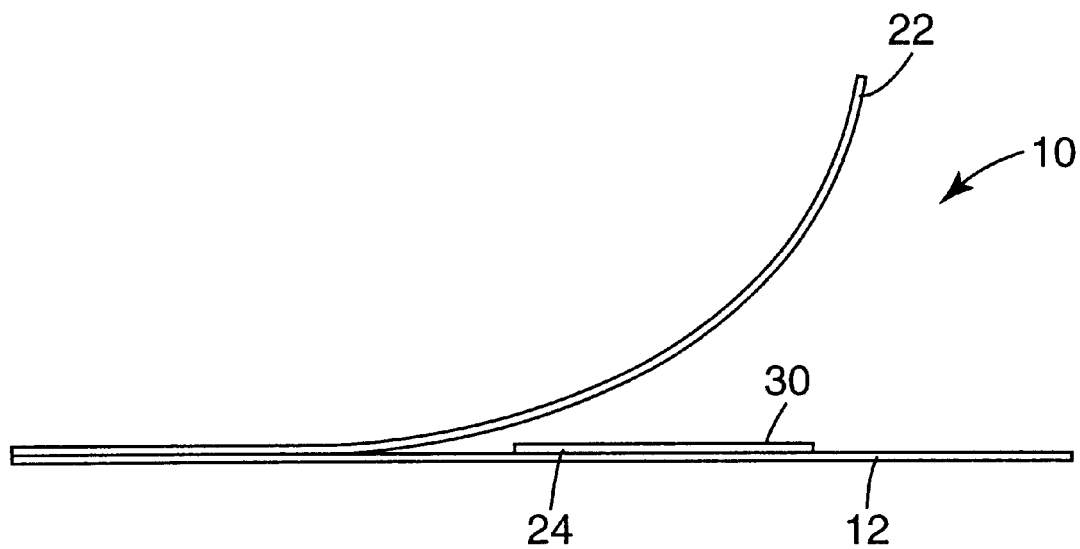
FIG. 3 is a side view of a third embodiment of the invention.
Figure 4:
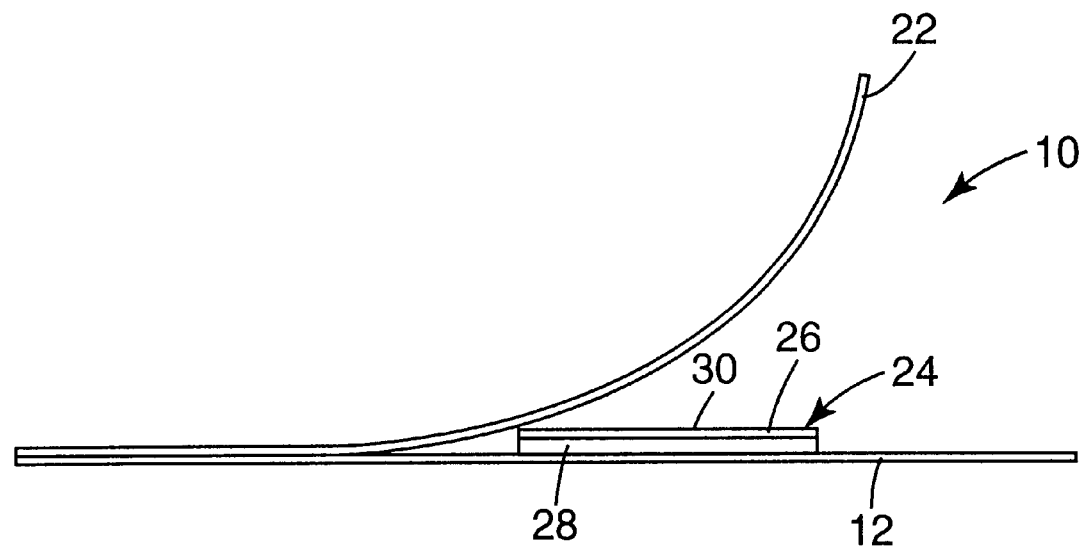
FIG. 4 is a side view of a fourth embodiment of the invention.

The pedestal 24 comprises a non-absorbent culture surface 30 onto which an aqueous sample is deposited. As used herein, "non-absorbent" describes the nature of the culture surface 30 prior to being coated with culture medium 16, if such a coating is desired. In one embodiment, shown in FIG. 3, the pedestal 24 comprises a non-absorbent material such that the culture surface 30 is the exposed top surface of the pedestal 24. In another embodiment, shown in FIG. 4, the pedestal 24 comprises a base layer 28 and a non-absorbent top layer 26. In one embodiment, the base layer 28 comprises polystyrene foam. However, the base layer 28 may be made from any suitable, supportive material, absorbent or non-absorbent, rigid or flexible, so long as it does not interfere with the growth of microorganisms on the culture surface 30. In the embodiment shown in FIG. 4, the culture surface 30 comprises the non-absorbent layer 26. The non-absorbent layer 26 comprises any suitable material which will not absorb the aqueous sample and which will not interfere with the growth of microorganisms. Suitable materials for the non-absorbent layer 26 include films of polyester, polypropylene or polystyrene. Other suitable embodiments for the non-absorbent layer 26 include, but are not limited to, waterproof coatings such as polyethylene film, pressure-sensitive adhesives, wax coatings, metal foils, and the like.

The claimed device permits culturing an aqueous sample so that spreading of the aqueous sample is self-limited by the claimed device. After the aqueous sample is deposited on the culture surface 30, no further manipulation of the sample is required to uniformly spread the sample to the edge of the culture surface 30. An appropriate volume of aqueous sample is placed on the culture surface 30 and the cover sheet 22 is lowered so that it completely covers the culture surface 30. As the cover sheet 22 is lowered, the aqueous sample spreads across the culture surface 30. When the edge of the aqueous sample reaches the edge of the culture surface 30, the pedestal 24 configuration of the claimed invention prevents further spreading of the sample. Thus, the cover sheet 22 and the pedestal 24 work in concert to deliver the benefits of the claimed invention. First, lowering the cover sheet 22 spreads the aqueous sample across the culture surface 30. Second, the pedestal confines the spreading of the aqueous sample to the edges of the culture surface 30. Moreover, the spreading and containment of the sample is achieved without additional equipment or manipulation of the aqueous sample by the end user.

The pedestal 24 may be any suitable height sufficient to limit spreading of the aqueous sample. Similarly, the diameter of the pedestal 24 may be any diameter suitable for constraining the spread of the desired volume of aqueous sample. One skilled in the art will be able to select an appropriate height and diameter for the pedestal 24 based, in part, on such factors as the sample viscosity, sample volume and hydration of the culture medium. The volume of aqueous sample deposited on the culture surface 30 may be any volume suitable for uniform spreading across the culture surface 30. In one embodiment, a volume from about 1 ml to about 5 ml of aqueous culture is used. One skilled in the art will be able to select an appropriate volume based, in part, on such factors as the viscosity of the sample, the diameter of the pedestal, the number of microorganisms in the sample and the desired colony density of the culture after incubation. Depending upon the volume of aqueous sample selected, the inoculum may or may not spread to the entire circumference of the culture surface edge. Likewise, the inoculum may or may not cover the entire culture surface 30.

The cover sheet 22 is attached to the substrate 12 such as by an adhesive, although any means of attachment is acceptable. In one embodiment, the cover sheet 22 comprises a polypropylene film. However, other materials having the desired qualities for a particular application may be used. The cover sheet 22 may be transparent to permit observation and counting of colonies of microorganisms growing on the culture surface 30. The cover sheet 22, at least where it is in contact with the aqueous sample, should be non-absorbent. In one embodiment, the entire cover sheet 22 can be made from water-insoluble material. Alternatively, the cover sheet 22 can be made from a water-soluble material and comprise a water-insoluble coating. The water-insoluble coating may cover the entire bottom surface of the cover sheet 22 or be limited to the area of the bottom surface of the cover sheet that could contact the aqueous sample deposited on the culture surface 30.

The cover sheet 22 should be substantially impermeable to microorganisms, thereby limiting the possibility that the dehydrated culture medium will be contaminated during shipping, storage and use of the claimed invention. This will also serve to limit contamination of the environment beyond the device 10 by microorganisms growing on the culture surface 30. The cover sheet 22 should also be substantially impermeable to water vapor, thereby providing an environment conducive for the growth of microorganisms during the incubation period. The material of the cover sheet 22 can be selected to provide the desired characteristics for a particular application. Examples of materials appropriate for various applications are disclosed in U.S. Pat. No. 4,565,783 (Hansen).

A culture medium 16 is adhered to the culture surface 30, the bottom surface of the cover sheet 22, or both. The culture medium is cold-water-soluble and comprises a gelling agent 18, one or more nutrients 20, both, or any combination thereof. As used herein, cold-water-soluble includes any material capable of forming a solution in water at about room temperature.

Suitable gelling agents for use in the culture medium 16 include natural and synthetic gelling agents that form a gel in water at about room temperature. Useful gelling agents include, but are not limited to, guar gum, xanthan gum, hydroxyethyl cellulose, carboxymethyl cellulose, polyacrylamide, locust bean gum, algin, and combinations thereof. A sufficient amount of gelling agent 18 is adhered to the culture surface 30, the bottom surface of the cover sheet 22, or both so that a gel will form when a predetermined volume of water or aqueous sample contacts the gelling agent 18. Specific characteristics of suitable gelling agents are disclosed in U.S. Pat. No. 4,565,783 (Hansen).

Nutrients suitable for use in the culture medium 16 include any substance or combination of substances that promotes the growth of microorganisms. Such substances may include, without limitation, carbohydrates, sugars, proteins, amino acids, enzymes, lipids, nucleic acids, nucleotides, oligonucleotides, salts and any combinations thereof. Combinations of nutrients useful for promoting growth of particular microorganisms are well known and one skilled in the art is able to select a combination of nutrients suitable for growing any desired microorganism or combination of microorganisms.

Suitable indicators for use in the device 10 include, but are not limited to, pH indicators and metabolic indicators, and any combinations thereof. The indicators may indicate the presence of microorganisms on the device by causing a color change, fluorescence, any other detectable effect, or any combination thereof.

The device 10 may also comprise one or more antibiotics selected to inhibit the growth of one or more species of bacteria, fungi, molds, or other microorganisms. As used herein, an antibiotic inhibits growth of a microorganism if it kills the microorganism or slows or prevents growth of the microorganism. The one or more antibiotics are adhered to the culture surface 30, the bottom surface of the cover sheet 22, or both. Efficacy of antibiotics against particular microorganisms is well known and one skilled in the art is able to select antibiotics to inhibit growth of undesired microorganisms while allowing growth of microorganisms desired for a particular test.

The culture medium 16, one or more indicators (if present), and one or more antibiotics (if present) are adhered to the desired surface of the device 10 by any suitable means. Suitable means for adhering the culture medium 16 to the desired surface or surfaces include, but are not limited to, broth coating and use of an adhesive. For broth coating, the culture medium 16, one or more indicators (if present) and one or more antibiotics (if present) are mixed with water, then deposited onto the surface to be coated. The coated film is heated to evaporate the water, leaving a coating of dehydrated culture medium adhered to the surface. Alternatively, the culture medium may be adhered to the desired surface by use of an adhesive such as those disclosed in U.S. Pat. No. 4,565,783 (Hansen). When an adhesive is used, the culture medium 16, one or more indicators (if present) and one or more antibiotics (if present) may be adhered to the surface of the adhesive or incorporated within the adhesive.

FIG. 1 shows an embodiment of the claimed invention in which the culture medium 16 is adhered to the bottom surface of the cover sheet 22 with adhesive 14. In this embodiment, at least some of the culture medium 16 should be located on a portion of the bottom surface of the cover sheet 22 that may contact water or aqueous sample deposited on the culture surface 30. FIG. 2 shows an embodiment of the claimed invention in which the culture medium 16 is adhered to the culture surface 30 with adhesive 14.

Additional embodiments (not shown) include those in which culture medium 16 comprises either a gelling agent 18 or the one or more nutrients 20, but not both. Still other embodiments include all other combinations having the gelling agent 18 adhered to the bottom surface of the cover sheet 22, the culture surface 30 or both, and also having the one or more nutrients 20 adhered to the bottom surface of the cover sheet 22, the culture surface 30 or both. The gelling agent 18 and the one or more nutrients 20 may be adhered to the same surface or different surfaces. Any indicator, if present, may be adhered to either surface without regard to the surface or surfaces on which the culture medium is adhered. Similarly, antibiotics, if present, may be adhered to either surface without regard to the surface or surfaces on which the culture medium is adhered. Also, in embodiments comprising more than one nutrient, each nutrient may be adhered to either surface without regard to the surface on which other nutrients or other constituents of the culture medium are adhered.

The complete disclosures of the patents, patent documents and publications cited herein are expressly incorporated herein by reference in their entirely into this disclosure as if each had been individually incorporated.

EXAMPLES

The following examples are provided as illustrative of the claimed invention and are not to be construed to limit the scope of the claimed invention to the particular examples or embodiments disclosed as follows. Unless otherwise indicated, all parts and percentages are by weight Example 1

Assay Device with Elevated Sample-Receiving Surface

An assay device having an elevated film surface for receiving and spreading of a liquid sample was constructed as described in this example. The assay device is capable of being used for the detection and enumeration of microorganisms in a liquid test sample.

A mixture of Bacto™ Tryptic Soy Broth (30 g, Becton Dickinson, Sparks, Md.), Guar Bean Gum (3.3 g, Rhodia, Kreuzlinger, Switzerland), and water (300 ml) was coated at a thickness of 0.25 mm wet (dry coating weight of 20 g/m$^2$) onto 0.19-mm polyester film (Dupont, Wilmington, Del.) and the resulting coated film heated at 100° C. to evaporate the water. The non-coated side of the polyester film was laminated by hand to a sheet of polyacrylate pressure sensitive adhesive (PSA) (3M Grade 467, 3M Company, St. Paul, Minn.) that in turn was laminated by hand to 0.51-mm polystyrene foam (Owens Ill., Bardstown, Ky.), that in turn was laminated by hand to another sheet of the polyacrylate PSA. From the resulting laminate (coated-film/PSA/foam/PSA) was die-cut a cylinder (5.1-cm diameter, 0.79-mm height) that was then adhered (PSA side down) to a rectangular sheet (7.6-cm×10.2-cm) of 0.19-mm polyester film. The top film (7.6-cm×10.2-cm) of a Petrifilm™ Aerobic Count Plate (3M Company, St. Paul, Minn. was adhered to an edge of the polyester sheet with the aid of double-stick tape. (This top film was adhesive-coated polypropylene film with the adhesive containing 2,3,5-triphenyl tetrazolium chloride (TTC) indicator and the adhesive dusted with guar gum.)

The assay device was evaluated as follows. The top film was lifted and a 1.0-ml sample of sterile standard method buffer was pipetted onto the center of the nutrient-coated circular film surface. The top film was then closed on top of the sample and, with no external pressure, the liquid sample flowed to the edge of the film circle and stopped. None of the sample flowed beyond the edge of the circle.

Example 2

Assay Device with Elevated Sample-Receiving Surface

An assay device having an elevated film surface for receiving and spreading of a liquid sample was constructed as described in Example 1, except that the polystyrene foam layer was not used. Therefore, the resulting device had a cylinder with a height of about 0.20 mm in contrast to the Example 1 cylinder that had a height of about 0.79 mm. The Example 2 device was then inoculated with a 1.0-ml liquid sample of buffer solution as described in Example 1. The top film was then closed on top of the sample and, with no external pressure, the liquid sample flowed to the edge of the film circle. At one portion of the film circle the liquid flowed beyond the edge to form a small "nodule", i.e., a portion of liquid sample outside the circumference of the film circle.

The results of this example suggest that the height of the assay device cylinder is an important parameter in having an elevated sample-receiving surface that will retain a liquid sample without the sample flowing beyond the top edge of the cylinder.

Example 3

Detection and Enumeration of *Staphylococcus Aureus*

An assay device having an elevated film surface for receiving and spreading of a liquid sample was constructed as described in Example 1. The device was then inoculated as described in Example 1 with a 1.0-ml liquid sample of pure culture *E. Coli* [ATCC 11229 diluted with Butterfield's Phosphate Buffer (Weber Scientific, Hamilton, N.J.)]. As in Example 1, the liquid sample flowed to the edge of the film circle and stopped. The inoculated assay device was then incubated at 32° C. for 48 hours, after which 66 cfu/ml were counted.

Example 4

Detection and Enumeration of Microorganisms in a Milk Sample

An assay device having an elevated film surface for receiving and spreading of a liquid sample was constructed as described in Example 1. The device was then inoculated as described in Example 1 with a 1.0-ml sample of skim milk. As in Example 1, the liquid sample flowed to the edge of the film circle and stopped. The inoculated assay device was then incubated at 32° C. for 48 hours, after which 44 cfu/ml were counted.

Various modifications and alterations to this invention will become apparent to one skilled in the art without departing from the scope and spirit of the invention. The preceding examples are offered to aid in understanding the features, advantages and other details of the present invention and are presented by way of example only. It should be expressly understood that particular ingredients and amounts used as well as other conditions and details are not to be construed in a manner that would unduly limit the scope of the invention. The scope of the invention is intended to be limited only by the claims as set forth herein as follows.

What is claimed is:

1. A device for growing microorganisms comprising:
   a substrate having a top side;
   a pedestal mounted on the top side of the substrate and comprising a non-absorbent culture surface;
   a flexible cover sheet attached to the substrate and comprising a bottom surface; and
   a culture medium deposited on one or more surfaces selected from:
   the culture surface, and
   the cover sheet bottom surface.

2. The device of claim 1 wherein the culture medium comprises a cold-water-soluble gelling agent, one or more nutrients, or a combination thereof.

3. The device of claim 1 wherein the substrate is a flexible sheet.

4. The device of claim 1 wherein the substrate is a rigid base.

5. The device of claim 1 wherein the cover sheet is transparent.

6. The device of claim 1 wherein the pedestal comprises non-absorbent material.

7. The device of claim 1 wherein the pedestal comprises:
  a pedestal base, and
  a layer of non-absorbent material comprising the culture surface.

8. The device of claim 1 wherein the substrate and the pedestal are transparent.

9. The device of claim 1 wherein the culture medium is selected to promote the growth of fungi.

10. The device of claim 1 wherein the culture medium is selected to promote the growth of molds.

11. The device of claim 1 wherein the culture medium is selected to promote the growth of bacteria.

12. The device of claim 1 wherein the gelling agent is guar gum, xanthan gum, hydroxyethyl cellulose, carboxymethyl cellulose, polyacrylamide, locust bean gum, algin, or a combination thereof.

13. The device of claim 1 further comprising an indicator.

14. The device of claim 2 wherein at least one of the one or more nutrients is dehydrated.

15. The device of claim 1 further comprising an antibiotic.

16. A method of culturing microorganisms comprising:
  providing a device for growing microorganisms comprising:
    a substrate having a top side,
    a pedestal mounted on the top side of the substrate and comprising a non-absorbent culture surface,
    a flexible cover sheet attached to the substrate and comprising a bottom surface, and
    a culture medium deposited on one or more surfaces selected from:
      the culture surface, and
      the cover sheet bottom surface;
  placing a sample on the culture surface;
  covering the sample with the cover sheet; and
  incubating the device.

17. The method of claim 16 wherein the culture medium comprises a cold-water-soluble gelling agent, one or more nutrients, or a combination thereof.

18. A method of detecting microorganisms comprising:
  providing a device for growing microorganisms comprising:
    a substrate having a top side,
    a pedestal mounted on the top side of the substrate and comprising a non-absorbent culture surface,
    a flexible cover sheet attached to the substrate and comprising a bottom surface, and
    a culture medium deposited on one or more surfaces selected from:
      the culture surface, and
      the cover sheet bottom surface;
  placing a sample on the culture surface;
  covering the sample with the cover sheet;
  incubating the device; and
  detecting the microorganisms.

19. The method of claim 18 wherein the culture medium comprises a cold-water-soluble gelling agent, one or more nutrients, or a combination thereof.

20. The method of claim 18 wherein the culture medium further comprises an indicator.

* * * * *

UNITED STATES PATENT AND TRADEMARK OFFICE
CERTIFICATE OF CORRECTION

PATENT NO. : 6,632,661 B2
DATED : October 14, 2003
INVENTOR(S) : Peter D. Wickert It is certified that error appears in the above-identified patent and that said Letters Patent is hereby corrected as shown below:

Title page,
Item [56], References Cited, U.S. PATENT DOCUMENTS, please add:
-- 4,476,226    10/1984    Hansen et al. --.
OTHER PUBLICATIONS, please delete:
-- US 4,476,226    10/1984    Hansen et al. (withdrawn) --

Signed and Sealed this

Thirtieth Day of March, 2004

JON W. DUDAS
*Acting Director of the United States Patent and Trademark Office*